(12) United States Patent
Holscher et al.

(10) Patent No.: US 6,191,127 B1
(45) Date of Patent: Feb. 20, 2001

(54) SUBSTITUTED HETEROCYCLES AND THEIR USE IN MEDICAMENTS

(75) Inventors: Peter Holscher; Hartmut Rehwinkel; Detlev Suelzle; Gerardine Burton; Margrit Hillmann; Iris Pribilla, all of Berlin (DE); David Daniel Davey, El Sobrante, CA (US)

(73) Assignee: Schering Aktiengesellschaft, Berlin (DE)

( * ) Notice: Under 35 U.S.C. 154(b), the term of this patent shall be extended for 0 days.

(21) Appl. No.: 09/423,072

(22) PCT Filed: Apr. 30, 1998

(86) PCT No.: PCT/DE98/01241
§ 371 Date: Nov. 1, 1999
§ 102(e) Date: Nov. 1, 1999

(87) PCT Pub. No.: WO98/50372
PCT Pub. Date: Nov. 12, 1998

(30) Foreign Application Priority Data

May 2, 1997 (DE) ................................ 197 20 155

(51) Int. Cl.[7] .................. A61K 31/536; A61K 31/5415; C07D 265/36; C07D 279/16
(52) U.S. Cl. ..................... 514/224.2; 514/230.5; 544/6; 544/51; 544/52; 544/71; 544/105
(58) Field of Search .................. 544/6, 51, 52, 544/71, 105; 514/224.2, 230.5

(56) References Cited

U.S. PATENT DOCUMENTS 5,629,322   5/1997  Guthikonda et al. ............. 514/313

FOREIGN PATENT DOCUMENTS 2169280   2/1995  (CA) .
09124626 * 5/1997  (JP) .
9505363   2/1995  (WO) .
9614844   5/1996  (WO) .

OTHER PUBLICATIONS

Raddatz et al., Chemical Abstracts, vol. 131, abstract 144608, 1999.*
Quast et al., Chemical Abstracts, vol. 118, abstract 124502, 1993.*
Shridhar et al., Chemical Abstracts, vol. 107, abstract 58948, 1987.*
Moderhack et al., Chemical Abstracts, vol. 106, abstract 32889, 1987.*
Chemical Abstracts, vol. 127, No. 3, Jul. 21, 1997, abstract No. 34228: Miyakoshi et al.

* cited by examiner

Primary Examiner—Richard L. Raymond
(74) Attorney, Agent, or Firm—Millen, White, Zelano & Branigan, P.C.

(57) ABSTRACT

Compounds of Formula I

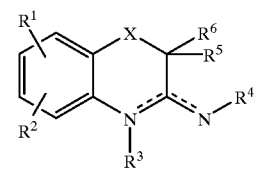

wherein X and $R^{1-6}$, are as defined herein, tautomeric forms thereof, and isomeric forms thereof, and salts thereof, are suitable for treating diseases that are induced by the action of nitrogen monooxide at pathological concentration. Such diseases include neurodegenerative diseases, inflammatory diseases, auto-immune diseases, and cardiovascular diseases.

46 Claims, No Drawings

SUBSTITUTED HETEROCYCLES AND THEIR USE IN MEDICAMENTS

This applicaition is a 371 of PCT/DE98/01241, filed Apr. 30, 1998.

The invention relates to substituted heterocycles, the process for their production and their use in pharmaceutical agents.

In human cells, there exist 3 specific forms of nitrogen monoxide synthases, which convert arginine into nitrogen monoxide (NO) and citrulline. Two constitutive NO-synthases (NOS) were identified that are present as $Ca^{++}$/calmodulin-dependent enzymes in the brain (bcNOS or NOS 1) or in the endothelium (ecNOS or NOS 3). The third isoform is the inducible NOS (iNOS or NOS 2), which is a $Ca^{++}$-independent enzyme and is induced after activation of different cells by endotoxin and cytokines.

NOS-inhibitors and especially specific inhibitors of NOS 1, NOS 2 or NOS 3 are therefore suitable for treatment of different diseases, which are induced or aggravated by pathological concentrations of NO in cells (Clin. Neuropharmac. 18, 1995 page 482).

As NOS-inhibitors, different compounds are described, such as, for example, cyclic amidine derivatives (WO 96/14844) or guanidine derivatives (WO95/05363).

It has now been found that the heterocycles that are substituted according to the invention can be used especially advantageously as pharmaceutical agents.

The invention relates to the compounds of Formula I, their tautomeric and isomeric forms and salts

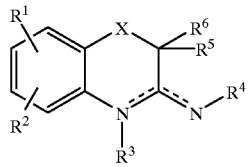

I in which

is a double bond,

X is —O— or —S(O)$_m$—,

R$^1$ and R$^2$, independently of one another, are hydrogen, halogen, S(O)$_n$—R$^7$, OR$^7$, COOR$^7$, NR$^7$R$^8$, C(=NR$^7$)—NHR$^8$, C$_{1-6}$ alkyl, C$_{2-6}$ alkenyl, C$_{2-6}$ alkynyl or —S—C(=NR$^7$)—NHR$^8$, R$^3$ and R$^4$, independently of one another, are hydrogen, C$_{1-12}$ alkyl, phenyl, CO—NR$^9$R$^{10}$, CSNR$^9$R$^{10}$, COR$^9$, CSR$^9$, COOR$^9$, OH, O—C$_{1-6}$ alkyl, and R$^5$ is halogen, C$_{1-8}$ alkoxy, S(O)$_p$—C$_{1-6}$ alkyl, C$_{1-8}$ alkylcarbonyl, C$_{1-8}$ alkyl, C$_{3-10}$ cycloalkyl, phenyl or a C$_{1-8}$ alkyl radical, which is substituted with phenyl, halogen, hydroxy, S(O)$_n$R$^{11}$, NO$_2$, OR$^{11}$, COOR$^{11}$, NR$^{11}$R$^{12}$, cyano, —C(=NR$^{11}$)—NHR$^{12}$ or —S—C(=NR$^{11}$)—NHR$^{12}$, R$^6$ is hydrogen or C$_{1-3}$ alkyl, which optionally together with R$^5$ forms a 3-, 4- or 5-membered spirocyclic compound, R$^7$, R$^8$ and R$^{11}$, R$^{12}$, the same or different, are hydrogen, C$_{1-6}$ alkyl, phenyl or C$_{3-7}$ cycloalkyl, R$^9$ and R$^{10}$, independently of one another, are hydrogen, phenyl, benzyl, C$_{3-7}$ cycloalkyl or C$_{1-6}$ alkyl, m, n, or p is 0, 1 or 2.

The compounds of Formula I, in which R$^3$ or R$^4$ means hydrogen, can be viewed as a preferred embodiment. Compounds in which R$^5$ is C$_{1-8}$ alkyl are another preferred embodiment. R$^6$ is preferably hydrogen. Especially preferred are compounds in which R$^3$, R$^4$ and R$^6$ mean hydrogen. The definition of m, n and p is preferably zero.

The compounds of Formula I can be present as tautomers, stereoisomers or geometric isomers. The invention also comprises all possible isomers, such as E- and Z-isomers, S- and R-enantiomers, diastereomers, racemates and mixtures thereof, including the tautomeric compounds of Formulas Ia and Ib

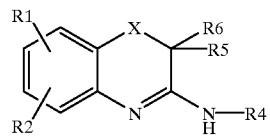

Ia

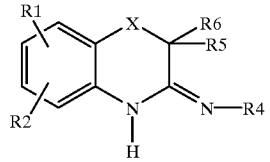

Ib

The physiologically compatible salts can be formed with inorganic and organic acids, such as, for example, oxalic acid, lactic acid, citric acid, fumaric acid, acetic acid, maleic acid, tartaric acid, phosphoric acid, HCl, HBr, sulfuric acid, p-toluenesulfonic acid, methanesulfonic acid, i.a.

For salt formation of acid groups, the inorganic or organic bases are also suitable, which are known for the formation of physiologically compatible salts, such as, for example, alkali hydroxides, such as sodium and potassium hydroxide, alkaline-earth hydroxides, such as calcium hydroxide, ammonia, amines such as ethanolamine, diethanolamine, triethanolamine, N-methylglucamine, tris-(hydroxymethyl)-methylamine, etc.

In each case, alkyl means a straight-chain or branched alkyl group, such as, e.g., methyl, ethyl, propyl, isopropyl, n-butyl, sec-butyl, tert-butyl, n-pentyl, sec-pentyl, tert-pentyl, neopentyl, n-hexyl, sec-hexyl, heptyl, octyl, preferably alkyl radicals with 1–4 C atoms. The alkenyl and alkynyl substituents are in each case straight-chain or branched. For example, the following radicals can be mentioned: vinyl, 2-propenyl, 1-propenyl, 2-butenyl, 1-butenyl, 2-butenyl, 1-methyl-1-propenyl, 2-methyl-2-propenyl, 3-methyl-2-propenyl, ethinyl, 1-propinyl, 2-propinyl, 1-butinyl, 2-butinyl.

Cycloalkyl is defined respectively as cyclopropyl, cyclobutyl, cyclopentyl, cyclohexyl or cycloheptyl.

Halogen means respectively fluorine, chlorine, bromine or iodine.

Aryl is defined respectively as naphthyl or phenyl.

For example, the following spirocyclic compounds can be mentioned: spiropropyl, spirobutyl, spiropentyl.

Alkyl radical R$^5$ can be substituted in one or more places with the above-mentioned substituents.

The invention also relates to the use of the compounds according to the invention for the production of a pharmaceutical agent for treating diseases, which are induced by the action of nitrogen monoxide at pathological concentrations. These include neurodegenerative diseases, inflammatory diseases, auto-immune diseases, and cardiovascular diseases.

For example, there can be mentioned:

Cerebral ischemia, hypoxia and other neurodegenerative diseases, which are brought into contact with inflammations, such as multiple sclerosis, amyotrophic lateral sclerosis and comparable sclerotic diseases, Parkinson's Disease, Huntington's Disease, Korksakoff's Disease, epilepsy, sleep disorders, schizophrenia, depression, migraine, hypoglycemia, dementia, such as, e.g., Alzheimer's Disease, HIV-dementia and presenile dementia.

They are also suitable for treating diseases of the cardiovascular system and for treating auto-immune and/or inflammatory diseases, such as hypotension, ARDS (adult respiratory distress syndrome), sepsis or septic shock, rheumatoid arthritis, osteoarthritis, insulin-dependent diabetes mellitus (IDDM), inflammatory disease of the pelvis/intestine (bowel disease), meningitis, glomerulonephritis, acute and chronic liver diseases, diseases by rejection (for example allogenic heart, kidney or liver transplants) or inflammatory skin diseases such as psoriasis, etc. Based on their profile of action, the compounds according to the invention are very well suited for specific inhibition of the neuronal NOS and can therefore be used for treating neurodegenerative diseases such as strokes.

To use the compounds according to the invention as pharmaceutical agents, they are brought into the form of a pharmaceutical preparation, which in addition to the active ingredient contains vehicles, adjuvants and/or additives that are suitable for enteral or parenteral administration. The administration can be done orally or sublingually as a solid in the form of capsules or tablets or as a liquid in the form of solutions, suspensions, elixirs, aerosols or emulsions or rectally in the form of suppositories or in the form of injection solutions that can also optionally be used subcutaneously, intramuscularly or intravenously, or topically or intrathecally. As adjuvants for the desired pharmaceutical agent formulation, the inert organic and inorganic support media that are known to one skilled in the art are suitable, such as, e.g., water, gelatin, gum arabic, lactose, starch, magnesium stearate, talc, plant oils, polyalkylene glycols, etc. Moreover, preservatives, stabilizers, wetting agents, emulsifiers or salts for changing the osmotic pressure or buffers can optionally be contained.

For parenteral administration, especially injection solutions or suspensions, especially aqueous solutions of the active compounds in polyhydroxyethylated castor oil, are suitable.

As vehicle systems, surface-active adjuvants such as salts of bile acids or animal or plant phospholipids, but also mixtures thereof as well as liposomes or their components can also be used.

For oral administration, especially tablets, coated tablets or capsules with talc and/or hydrocarbon vehicles or binders, such as, for example, lactose, corn or potato starch, are suitable. The administration can also be done in liquid form, such as, for example, as a juice, to which optionally a sweetener is added.

The dosage of the active ingredient can vary depending on method of administration, age and weight of the patient, type and severity of the disease that is to be treated and similar factors. The daily dose is 1–2000 mg, preferably 20–500 mg, whereby the dose can be given as an individual dose to be administered one time or divided into 2 or more daily doses.

The NOS-inhibitory action of the compounds of Formula I and their physiologically compatible salts can be determined with the variants that are mentioned below according to the methods by Bredt and Snyder in Proc. Natl. Acad. Sci. USA (1989) 86, 9030.

The action of the above-mentioned compounds is illustrated by the following examples.

| Substance | $IC_{50}$ bcNOS in $\mu M$ | $IC_{50}$ ecNOS in $\mu M$ | $IC_{50}$ iNOS in $\mu M$ |
|---|---|---|---|
| 2,8-Dimethyl-3-amino-1,4-benzoxazine | 20 | >100 | >10 |
| 2,6,7-Trimethyl-3-amino-1,4-benzoxazine | 3 | >10 | >100 |
| 2-n-Propyl-3-amino-1,4-benzoxazine | 1.2 | >10 | >100 |

Inhibition assay with recombinant human brain NO-synthases (bcNOS). (Concentration: 0.022 IU/l). Measured parameters: % inhibition by test compound. Substrate: [3H]-arginine (concentration 4.4E-08 mol/l). Analogously to recombinant human endothelial NO-synthases (ecNOS) and recombinant human inducible NO-synthases (iNOS).

The production of the compounds according to the invention is carried out in that a) a compound of Formula II or its salt

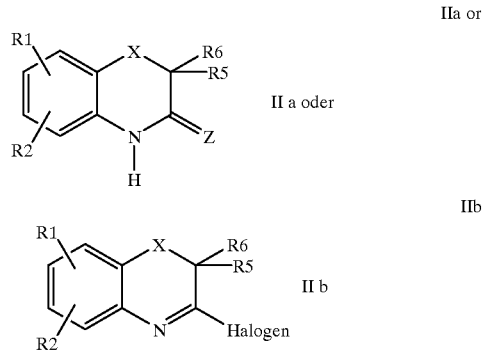

in which $R^1$, $R^2$ and X have the above meaning, and Z is oxygen or sulfur, is reacted with ammonia or primary or secondary amines, or b) a compound of Formula III

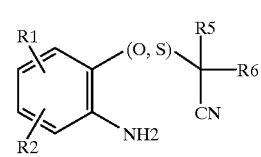

in which $R^1$, $R^2$, $R^5$ and $R^6$ have the above meaning, is cyclized and optionally then sulfides are oxidized, esters are saponified, acids are esterified, hydroxy groups are etherified or acylated, amines are acylated, alkylated, diazotized, halogenated, $NO_2$ is introduced or reduced, reacted with thiourea derivatives, the isomers are separated or the salts are formed.

The reaction according to process variant a) with ammonia is accomplished under pressure in an autoclave with excess ammonia at low temperatures (−78° C.) or by stirring in methanol that is saturated with ammonia. If it is reacted with amines, first iminoether or iminothioether is produced as an intermediate compound from lactam or thiolactam (e.g., with methyl iodide or methyl sulfate), and the latter is reacted with or without isolating the intermediate compound with the corresponding amines or their salts.

As an alternative, the compounds according to the invention can be obtained from aminonitriles according to process variant b), by being cyclized with a base, such as, e.g., alkali alcoholate.

The optionally subsequent saponification of an ester group can be carried out in a basic or acidic manner by being hydrolyzed at room temperature or at an elevated temperature to the boiling point of the reaction mixture in the presence of alkali hydroxides in ethanol or other alcohols or with use of acids, such as, e.g., hydrochloric acid, and optionally salts of aminobenzoxazines or -thiazines being further processed.

The esterification of carboxylic acid is done in a way that is known in the art with diazomethane or the corresponding alcohol in acid or in the presence of an activated acid derivative. As activated acid derivatives, for example, acid chloride, acid imidazolide or acid anhydride are suitable.

The synthesis of sulfoxides and sulfones is possible, for example, with peracids, such as m-chloroperbenzoic acid, in a known way. Halogenated side chains can be reacted to isothiourea derivatives with thioureas in the usual way.

In addition, a nitro group or halogen, especially bromine, can be introduced by electrophilic, aromatic substitution. Mixtures that are produced in this case can be separated in the usual way, also using HPLC. Compounds that are substituted with amidine are produced from nitrile by addition of amino compounds.

The reduction of the nitro group or optionally the cyano group to the amino group is carried out catalytically in polar solvents at room temperature or at an elevated temperature under hydrogen pressure. As catalysts, metals such as Raney nickel or noble metal catalysts such as palladium or platinum optionally in the presence of barium sulfate or on vehicles are suitable. Instead of hydrogen, ammonium formate can also be used in a known way. Reducing agents such as tin(II) chloride or titanium(III) chloride can also be used, such as complex metal hydrides, optionally in the presence of heavy metal salts. The ester group can advantageously be introduced before reduction. For nitro groups, reduction with zinc in acetic acid has proven its value.

If alkylation of an amino group is desired, alkylation can be performed with, for example, alkyl halides according to commonly used methods.

The acylation of the amino group is carried out in the usual way with, for example, an acid halide or acid anhydride, optionally in the presence of a base.

The introduction of the halogens chlorine, bromine or iodine via the amino group can also be carried out, for example, according to Sandmeyer, by the diazonium salts that are formed intermediately with nitrites being reacted with Cu(I) chloride or Cu(I) bromide in the presence of the corresponding acids such as hydrochloric acid or hydrobromic acid or being reacted with potassium iodide.

The introduction of an $NO_2$ group is possible by a number of known nitration methods. For example, nitration can be performed with nitronium tetrafluoroborate in inert solvents, such as halogenated hydrocarbons or in sulfolane or glacial acetic acid. Introduction by, e.g., nitrating acid in water or concentrated sulfur acid as a solvent is also possible at temperatures of between 0° C. and 30° C.

Hydroxy groups are esterified or etherified in a known way.

The isomer mixtures can be separated into enantiomers or E/Z-isomers according to commonly used methods, such as, for example, crystallization, chromatography or salt formation. The enantiomers can also be obtained by stereoselective syntheses or by separation according to individual reaction steps.

The production of the salts is carried out in the usual way, by a solution of the compound of Formula I being mixed with the equivalent amount of acid or excess acid, which optionally is in solution, and the precipitate being separated or the solution being worked up in the usual way.

If the production of the starting compounds is not described, the latter are known and commercially available or can be produced analogously to known compounds or according to processes that are described here.

The production of the lactams of Formula II can be carried out, for example, in that a compound of Formula IV

IV

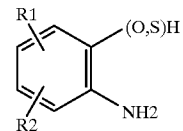

in which $R^1$ and $R^2$ have the above meaning, is reacted with a compound of Formula V

V

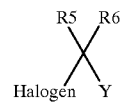

in which $R^5$ and $R^6$ have the above meaning, and Y is a reactive carboxyl group such as acid halide, nitrile or carboxylic acid ester, and is cyclized or in that a compound of Formula VI

VI

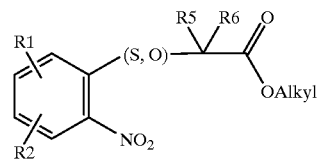

is cyclized after reduction.

New compounds were identified by one or more of the following methods: melting point, mass spectroscopy, infrared spectroscopy, nuclear magnetic resonance spectroscopy (NMR). NMR spectra were measured with a Bruker 300 MHz device; the (deuterated) solvents are respectively indicated and abbreviated as follows: $CDCl_3$ (chloroform), DMSO (dimethyl sulfoxide). Alterations are indicated in delta and ppm. In addition, THF means tetrahydrofuran, DMF means N,N-dimethylformamide, MeOH means methanol, and EE means ethyl acetate. All solvents are p.A. grade, unless otherwise indicated. All reactions are performed under protective gas, unless these are aqueous solutions. Here: mult. means multiplet, several signals; s means singlet; d means doublet; dd means double doublet, etc.; tr means triplet; H means hydrogen protons, J means coupling constants, ml means milliliters, and RT means room temperature. Melting points are indicated in degrees Celsius and are not corrected. The yields in percent relate to the educt, not to the conversion.

Below, the production of several precursors, intermediate products and products is described by way of example.

Starting Compounds

A) 2-Phenyl-2H-1,4-benzoxazin-3-one 2.18 g of 2-aminophenol is mixed in 13 ml of methyl-ethylketone with 4 g of sodium bicarbonate in 13 ml of water and mixed drop by drop at ice bath temperature with 3.63 ml of D,L-2-chloro-2-phenylacetyl chloride. After heating to 70° C., it is poured onto ice water, extracted with ethyl acetate, the organic phase is dried with magnesium sulfate and concentrated by evaporation. 6.3 g of crude product results, which is recrystallized from isopropyl ether.

Melting point 146° C.

B) 2,2-Dimethyl-1,4-benzoxazin-3-one 3 g of 2-aminophenol is mixed in 23 ml of toluene with 1.8 g of sodium hydride with the addition of 50 mg of TEBA (triethylbenzylammonium chloride), and 4.4 ml of 2-bromo-2-methylpropionic acid ethyl ester is added drop by drop at ice bath temperature. After 2 hours at room temperature, it is poured onto ice water, extracted with ethyl acetate, washed with brine, the organic phase is dried with magnesium sulfate and concentrated by evaporation. After recrystallization from isopropyl ether, 278 mg of crystals results.

[1H]-NMR (DMSO): 10.5 1H, 6.9 m 4H, 1.4 s 6H.

The following are produced in the same way:

2-Methyl-1 4-benzoxazin-3-one
from D,L-2-bromopropionic acid ethyl ester.
2-(2-Phenylethyl)-1,4-benzoxazin-3-one
[1H]-NMR (DMSO): 10.6 1H broad, 7.3–7.2 m 5H, 4.49 dd 1H, 2.8 m 2H, 2.1 m 2H.
2-Benzyl-1,4-benzoxazin-3-one
2-Ethyl-1,4-benzoxazin-3-one
[1H]-NMR (CDCl$_3$): 8.7 broad 1H, 7.0 to 6.8 m 4H, 4.52 dd 1H, 1.98 m 2H, 1.11 tr 3H.
2-Propyl-1,4-benzoxazin-3-one
[1H]-NMR (CDCl$_3$): 8.65 broad 1H, 7.0 to 6.8 m 4H, 4.59 dd 1H, 1.89 m 2H, 1.6 m 2H, 1.00 tr 3H.
2-(2-Propyl)-1,4-benzoxazin-3-one
2-tert-Butyl-1,4-benzoxazin-3-one
2-n-Butyl-1,4-benzoxazin-3-one
2-n-Hexyl-1,4-benzoxazin-3-one
2-Carboxymethyl-1,4-benzoxazin-3-one
2,2-spiro-Butyl-1,4-benzoxazin-3-one
2-Acetyl-1,4-benzoxazin-3-one

C) 2,6-Dimethyl-1,4-benzoxazin-3-one 3.39 g of 2-amino-4-methylphenol is mixed in 12 ml of toluene with 1.8 g of sodium hydride, and 3.95 ml of 2-bromo-propionic acid ethyl ether is added drop by drop at ice bath temperature. After 4 hours at room temperature, it is poured onto water, extracted with ethyl acetate, washed with brine, the organic phase is dried with magnesium sulfate and concentrated by evaporation. Column chromatography with hexane/ethyl acetate yields 43% product.

The following are produced in the same way:

2,5-Dimethyl-1,4-benzoxazin-3-one
2,7-Dimethyl-1,4-benzoxazin-3-one
2.8-Dimethyl-1,4-benzoxazin-3-one
2-Methyl-6-chloro-1,4-benzoxazin-3-one from 2-amino-4-chlorophenol
2-Methyl-7-methylcarboxy-1,4-benzoxazin-3-one
2-Methyl-6,8-dichloro-1,4-benzoxazin-3-one
2-Methyl-6-tert-butyl-1,4-benzoxazin-3-one
2,6,7-Trimethyl-1,4-benzoxazin-3-one
2,6,8-Trimethyl-1,4-benzoxazin-3-one

D) 2-Methyl-1,4-benzothiazin-3-one 2.95 g of 2-amino-thiophenol is mixed in 6 ml of toluene with 1.8 g of sodium hydride, and 3.95 ml of 2-bromo-propionic acid ethyl ether is added drop by drop at ice bath temperature. After 2 hours at room temperature, it is poured onto water, extracted with ethyl acetate, washed with brine, the organic phase is dried with magnesium sulfate and concentrated by evaporation.

Column chromatography with hexane/ethyl acetate yields the product. [1H]-NMR (CDCl$_3$): 8.83 s broad 1H, 7.32 dd 1H, 7.19 dtr 1H, 7.03 dtr 1H, 6.90 dd 1H, 3.57 q 1H, 1.51 d 3H.

The following are produced in the same way:
2-Ethyl-2H-1,4-benzothiazin-3-one
2-(2-Propyl)-2H-1,4-benzothiazin-3-one
[1H]-NMR (CDCl$_3$): 8.68 broad 1H, 7.3 to 6.8 plus 4H, 3.12 d 1H, 1.97 heptet 1H, 1.09 d 6H.
2-n-Propyl-2H-1,4-benzothiazin-3-one

E) 2-Phenyl-2-H-3-chloro-1,4-benzoxazine 0.1 ml of phosphorus oxychloride and 1.2 mmol of triethylamine are added to 0.22 g of 2-phenyl-1,4-benzoxazin-3-one in 3 ml of acetonitrile. After 12 hours of stirring at room temperature, it is concentrated by evaporation. The crude product can be used for further reactions.

The following are produced in the same way:
2-Methyl-3-chloro-1,4-benzoxazine
2,6-Dimethyl-3-chloro-1,4-benzoxazine
2-Methyl-3,6-dichloro-1,4-benzoxazine

F) 2-Ethyl-1,4-benzoxazine-3-thione 0.25 g of 2-ethyl-1,4-benzoxazin-3-one is stirred in 2 ml of pyridine with 95 mg of phosphorus pentasulfide. The reaction is completed by reflux-boiling. It is poured onto water, extracted with ethyl acetate, and the organic phase is washed with brine. It is dried with magnesium sulfate and concentrated by evaporation. After column chromatography with hexane/ethyl acetate, 220 mg of product results.

[1H]-NMR (CDCl$_3$) 7.09 to 6.8 m 4H, 4.39 dd 1H, 2.1 to 1.8 m 4H, 1.11 tr 3H.

The following are produced in the same way:
2,2-Dimethyl-1,4-benzoxazine-3-thione
The yield is 76%.
[1H]-NMR (CDCl$_3$): 9.8 broad 1H, 7.10 to 6.84 m 4H, 1.69 s 6H.
2-(2-Phenylethyl)-2H-1,4-benzoxazine-3-thione
[1H]-NMR (CDCl$_3$): 9.7 1H, 7.33 to 6.95 m 8H, 6.87 dd 1H<4.91 dd 1H, 2.9 m 2H, 2.4 and 2.2 m 1H each.
Melting point 134° C.
Yield 78%.
2-Phenyl-2H-1,4-benzoxazine-3-thione
[1H]-NMR (CDCl$_3$): 9.9 1H, 7.5 m 2H, 7.3 m 3H, 7.1 to 6.8 m 4H, 6.1 s 1H.

Melting point 191° C.

Yield 90[{]ps

2-Benzyl-1,4-benzoxazine-3-thione
2-Propyl-1,4-benzothiazine-3-thione
2-Propyl-1,4-benzoxazine-3-thione
2-Ethyl-1,4-benzothiazine-3-thione
2-(2-Propyl)-1,4-benzothiazine-3-thione
2-(2-Propyl)-1,4-benzoxazine-3-thione
2-tert-Butyl-1,4-benzoxazine-3-thione
2,5-Dimethyl-1,4-benzoxazine-3-thione
2,7-Dimethyl-1,4-benzoxazine-3-thione
2,8-Dimethyl-1,4-benzoxazine-3-thione
2,6-Dimethyl-1,4-benzoxazine-3-thione
2-n-Butyl-1,4-benzothiazine-3-thione
2-n-Butyl-1,4-benzoxazine-3-thione
2-n-Hexyl-1,4-benzoxazine-3-thione
2-Carboxymethyl-1,4-benzoxazine-3-thione
2,2-spiro-Butyl-1,4-benzoxazine-3-thione
2-Acetyl-1,4-benzoxazine-3-thione
2-Methyl-6-chloro-1,4-benzoxazine-3-thione
2-Methyl-7-methylcarboxy-1,4-benzoxazine-3-thione
2-Methyl-6,8-dichloro-1,4-benzoxazine-3-thione
2-Methyl-6-tert-butyl-1,4-benzoxazine-3-thione
2,6,7-Trimethyl-1,4-benzoxazine-3-thione
2,6,8-Trimethyl-1,4-benzoxazine-3-thione

G) 2-(2-Hydroxyethyl)-1,4-benzoxazin-3-one 2.18 g of 2-aminophenol and 1.1 equivalents of 2-bromo-γ-butyrolactone are mixed in 25 ml of DMF with 4 g of potassium carbonate. After 6 hours, it is heated to 75° C., poured onto water, extracted with ethyl acetate, the organic phase is dried with sodium sulfate and concentrated by evaporation. 40% yield results.

[1H]-NMR (DMSO): 10.6 broad 1H, 6.9 m 4H, 4.65 dd 1H, 4.52 broad 1H, 3.6 m 2H, 1.9 m 2H.

From this, the following is obtained in the above-described process with the use of a protective group:

2-(2-Hydroxyethyl)-1,4-benzoxazine-3-thione

H) 2-(2-Bromoethyl)-1,4-benzoxazin-3-one 580 mg of 2-(2-hydroxyethyl)-1,4-benzoxazin-3-one is stirred with 1 equivalent each of triphenylphosphine and tetrabromomethane in 50 ml of dichloromethane. After 12 hours at room temperature, the reaction is completed. The mixture is concentrated by evaporation, and all of this is put onto a column. After column chromatography, the title compound is obtained in a yield of 79%. [1H]-NMR (CDCl$_3$): 8.35 broad 1H, 7.05 to 6.8 m 4H, 4.77 dd 1H, 3.67 m 2H, 2.5 m 2H.

I) 2-(2-Methylthio-ethyl)-1,4-benzoxazin-3-one 586 mg of 2-(2-bromoethyl)-1,4-benzoxazin-3-one is mixed in a methanol-DMF mixture with 245 mg of sodium thiomethylate while being stirred. After 4 hours, it is concentrated by evaporation. After column chromatography, the title compound is obtained in a yield of 53%.

From this, the following is obtained in the above-described process:

2-(2-Methylthio-ethyl)-1,4-benzoxazine-3-thione

EXAMPLE 1

2-Methyl-3-amino-1,4-benzoxazine 2 g of 2-aminophenol is deprotonated in methanol with 1 equivalent of sodium methylate, and the solution is mixed drop by drop at ice bath temperature with 3 ml of D,L-2-chloro-2-methylacetonitrile. After the end of the alkylation reaction, it is heated with the addition of catalytic amounts of sodium methylate. It is poured onto water, extracted with ethyl acetate, the organic phase is dried with magnesium sulfate and concentrated by evaporation. 1.3 g of crude product, which is recrystallized, results.

[1H]-NMR (CDCl$_3$): 7.30 dd 1H, 6.94 dd 2H, 6.86 dd 1H, 5.05 broad 2H, 4.62 q 7 Hz 1H, 1.49 d 7 Hz 3H.

Melting point 153° C.

The same compound is obtained from thione analogously to Example 3.

EXAMPLE 2

2-Phenyl-2-H-3-amino-1,4-benzoxazine 1 mmol of 2-phenyl-2H-3-chloro-1,4-benzoxazine in 2 ml of acetonitrile is stirred at an ammonia pressure of 8 bar in an autoclave for several hours. It is concentrated by evaporation. The crude product is washed with water and dried with magnesium sulfate. Then, in addition to 2-phenyl-2H-4H-1,4-benzoxazin-3-one, a fraction of 45% product is obtained with use of column chromatography in ethyl acetate.

Melting point 232° C. decomposition.

The following are produced in the same way:

2,6-Dimethyl-3-amino-1,4-benzoxazine 2-Methyl-3-amino-6-chloro-1,4-benzoxazine

[1H]-NMR (CDCl$_3$): 7.01 d 1H, 6.90 dd 8/1 Hz 1H, 6.79 d 1H, 4.61 q 7 Hz, 1.49 d 3H. The yield is 46%.

EXAMPLE 3

2-Ethyl-3-amino-1,4-benzoxazine

The compound is obtained by stirring 210 mg of 2-ethyl-1,4-benzoxazine-3-thione in 15 ml of saturated ammonia solution in methanol after 2 days at room temperature. The crude product is purified by column chromatography after concentration by evaporation. 144 mg of product results.

[1H]-NMR (CDCl$_3$): 7.05 to 6.82 m 4H, 4.41 dd 1H, 1.9 to 1.6 m 4H, 1.07 tr 3H.

The following are produced in the same way:

2,2-Dimethyl-3-amino-1,4-benzoxazine

[1H]-NMR (CDCl$_3$): 7.03 to 6.81 m 4H, 1.50 s 6H.

Melting point 202° C.

66% yield.

2,7-Dimethyl-3-amino-1,4-benzoxazine
2,8-Dimethyl-3-amino-1,4-benzoxazine
2,5-Dimethyl-3-amino-1,4-benzoxazine
2,6-Dimethyl-3-amino-1,4-benzoxazine
2-(2-Phenylethyl)-2H-3-amino-1,4-benzoxazine Colorless oil. The yield is 83%.

2-Methyl-3-amino-7-carboxymethyl-1,4-benzoxazine

[1H]-NMR (DMSO): 7.49 dd, 7.30 d, 7.1 s broad, 6.90 d 1H each, 4.72 q 1H, 3.8 s 3H, 1.29 d 3H.

2-Methyl-3-amino-6,8-dichloro-1,4-benzoxazine
2-Benzyl-3-amino-1,4-benzoxazine
2-Propyl-3-amino-1,4-benzothiazine
2-Propyl-3-amino-1,4-benzoxazine

[1H]-NMR (CDCl$_3$): 7.1 to 6.8 m 4H, 4.50 dd 1H, 1.9 to 1.5 m 4H, 0.99 tr 3H.

2-(2-Propyl)-3-amino-1,4-benzothiazine

[1H]-NMR (DMSO): 6.7 broad, 7.2 to 6.75 plus 4H, 3.02 d 1H, 1.51 heptet 1H, 0.91 dd 6H.

2-(2-Propyl)-3-amino-1,4-benzoxazine

[1H]-NMR (DMSO): 6.7 broad, 6.75 m 4H, 4.22 d 1H, 1.90 heptet 1H, 0.99 d 3H, 0.88 d 3H.

2-n-Butyl-3-amino-1,4-benzothiazine
2-n-Butyl-3-amino-1,4-benzoxazine
2-tert-Butyl-3-amino-1,4-benzoxazine
2-n-Butyl-3-amino-1,4-benzoxazine
2-Ethyl-3-amino-1,4-benzothiazine
2-Methyl-3-amino-6-tert-butyl-1,4-benzoxazine
Melting point: 125–130° C.
2,6,7-Trimethyl-3-amino-1,4-benzoxazine of semi-congealed oil
2,6,8-Trimethyl-3-amino-1,4-benzoxazine
2-n-Hexyl-3-amino-1,4-benzoxazine
2-Carboxymethyl-3-amino-1,4-benzoxazine
2,2-spiro-Butyl-3-amino-1,4-benzoxazine

[1H]-NMR (MeOH): 6.9 to 6.7 m 4H, 2.45, 2.20, 1.84 m 2H each.

2-(2-Hydroxyethyl)-3-amino-1,4-benzoxazine
2-(2-Methylthio-ethyl)-3-amino-1,4-benzoxazine.

[1H]-NMR (CDCl$_3$): 7.05 to 6.83 m 4H, 4.77 dd 1H, 2.70 m 2H, 2.11 s 3H, 2 to 1.8 m 2H

EXAMPLE 4

2-(S)-Methyl-3-amino-6-chloro-1,4-benzoxazine and 2-(R)-methyl-3-amino-6-chloro-1,4-benzoxazine Several milligrams of 2-(R,S)-methyl-3-amino-6-chloro-1,4-benzoxazine are eluted on a chiral HPLC column (Chirapak AD, 250×4.6) with hexane/isopropanol/ethanol at 1 ml/minute and detected at 220 nm. Two fractions are collected.

EXAMPLE 5

2-Methyl-3-amino-6-chloro-1,4-benzoxazine-hydrochloride 1.0 ml of ethereal 1N hydrochloric acid is added to 0.051 g of 2-methyl-3-amino-6-chloro-1,4-benzoxazine in THF at ice bath temperature. Stirring is repeated, and it is allowed to stand for some time. The crystals are separated by decanting. The yield is 67%.

[1H]-NMR (DMSO): 10.1 s broad 1H, 7.36 d 1H, 7.19 dd 1H, 7.09 d 1H, 5.33 q 1H, 1.51 d 3H.

What is claimed is:

1. A compound of Formula I

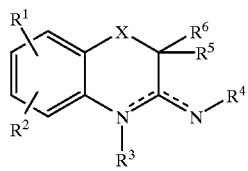

I wherein

is a double bond;

X is —O— or —S(O)$_m$—;

R$^1$ and R$^2$, independently of one another, are each hydrogen, halogen, S(O)$_n$—R$^7$, OR$^7$, COOR$^7$, NR$^7$R$^8$, C(=NR$^7$)—NHR$^8$, C$_{1-6}$ alkyl, C$_{2-6}$ alkenyl, C$_{2-6}$ alkynyl or —S—C(=NR$^7$)—NHR$^8$;

R$^3$ and R$^4$, independently of one another, are each hydrogen, C$_{1-12}$ alkyl, phenyl, CO—NR$^9$R$^{10}$, CSNR$^9$R$^{10}$, COR$^9$, CSR$^9$, COOR$^9$, OH, or O—C$_{1-6}$ alkyl;

R$^5$ is halogen, C$_{1-8}$ alkoxy, S(O)$_p$—C$_{1-6}$ alkyl, C$_{1-8}$ alkylcarbonyl, methyl, ethyl, propyl, isopropyl, n-butyl, sec-pentyl, tert-pentyl, neo-pentyl, n-hexyl, sec-hexyl, heptyl, octyl, C$_{3-10}$ cycloalkyl, phenyl or a C$_{1-8}$ alkyl radical, which is substituted with phenyl, halogen, hydroxy, S(O)$_n$R$^{11}$, NO$_2$, OR$^{11}$, COOR$^{11}$, NR$^{11}$R$^{12}$, cyano, —C(=NR$^{11}$)—NHR$^{12}$ or —S—C(=NR$^{11}$)—NHR$^{12}$;

R$^6$ is hydrogen or C$_{1-3}$ alkyl, which optionally together with R$^5$ forms a 3-, 4- or 5-membered spirocyclic compound;

R$^7$, R$^8$ and R$^{11}$, R$^{12}$, being the same or different, are each hydrogen, C$_{1-6}$ alkyl, phenyl or C$_{3-7}$ cycloalkyl;

R$^9$ and R$^{10}$, independently of one another, are each hydrogen, phenyl, benzyl, C$_{3-7}$ cycloalkyl or C$_{1-6}$ alkyl; and m, n, or p is 0, 1 or 2; or a physiologically compatible salt thereof, with the proviso that when R$^1$, R$^2$, R$^3$, R$^4$ and R$^6$ are each H, R$^5$ is not C$_{1-8}$ alkoxy.

2. A compound according to claim 1, wherein R$^3$ or R$^4$ is hydrogen.

3. A compound according to claim 1, wherein R$^6$ is hydrogen.

4. A compound according to claim 1, wherein R$^5$ is methyl, ethyl, propyl, isopropyl, n-butyl, sec-pentyl, tert-pentyl, neo-pentyl, n-hexyl, sec-hexyl, heptyl, or octyl.

5. A compound according to claim 1, wherein said compound is:

2,6-Dimethyl-3-amino-1,4-benzoxazine or a physiologically compatible salt thereof;
2,5-Dimethyl-3-amino-1,4-benzoxazine or a physiologically compatible salt thereof;
2,7-Dimethyl-3-amino-1,4-benzoxazine or a physiologically compatible salt thereof;
2,8-Dimethyl-3-amino-1,4-benzoxazine or physiologically compatible salt thereof;
2-Methyl-2H-3-amino-1,4-benzoxazine or a physiologically compatible salt thereof;
2-Methyl-2H-3-amino-1,4-benzothiazine or a physiologically compatible salt thereof;
2-Ethyl-3-amino-1,4-benzothiazine or a physiologically compatible salt thereof;
2-Ethyl-3-amino-1,4-benzoxazine or a physiologically compatible salt thereof;
2-n-Propyl-3-amino-1,4-benzoxazine or a physiologically compatible salt thereof;
2-Phenyl-2-H-3-amino-1,4-benzoxazine or a physiologically compatible salt thereof;
2-(2-hydroxyethyl)-3-amino-1,4-benzoxazine or a physiologically compatible salt thereof;
2-(2-bromoethyl)-3-amino-1,4-benzoxazine or a physiologically compatible salt thereof; or
2-(2-methylthio-ethyl)-3-amino-1,4-benzoxazine or a physiologically compatible salt thereof.

6. A compound according to claim 2, wherein R$^6$ is hydrogen.

7. A compound according to claim 2, wherein R$^5$ is methyl, ethyl, propyl, isopropyl, n-butyl, sec-pentyl, tert-pentyl, neo-pentyl, n-hexyl, sec-hexyl, heptyl, or octyl.

8. A compound according to claim 3, wherein $R^5$ is methyl, ethyl, propyl, isopropyl, n-butyl, sec-pentyl, tert-pentyl, neo-pentyl, n-hexyl, sec-hexyl, heptyl, or octyl.

9. A compound according to claim 1, wherein X is —O—.

10. A compound according to claim 1, wherein X is —S—.

11. A compound according to claim 1, wherein said compound is a tautomeric compound of Formula Ia

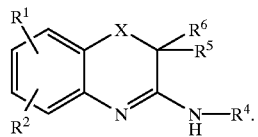

Ia

12. A compound according to claim 1, wherein said compound is a tautomeric compound of Formula Ib

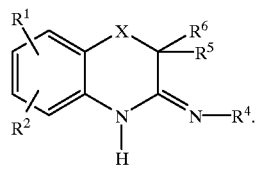

Ib

13. A compound according to claim 1, wherein $R^3$, $R^4$, and $R^6$ are each hydrogen.

14. A compound according to claim 1, wherein m, n, and p are each zero.

15. A compound according to claim 1, wherein $R^5$ and $R^6$ together form spiropropyl, spirobutyl or spiropentyl.

16. A compound according to claim 1, wherein said compound is an S-enantiomer.

17. A compound according to claim 1, wherein said compound is an R-enantiomer.

18. A compound according to claim 1, wherein at least one of $R^1$ and $R^2$ is methyl, ethyl, propyl, isopropyl, n-butyl, sec-butyl, tert-butyl, n-pentyl, sec-pentyl, tert-pentyl, neopentyl, n-hexyl, sec-hexyl, heptyl, octyl, vinyl, 2-propenyl, 1-propenyl, 2-butenyl, 1-butenyl, 2-butenyl, 1-methyl-1-propenyl, 2-methyl-2-propenyl, 3-methyl-2-propenyl, ethinyl, 1-propinyl, 2-propinyl, 1-butinyl, or 2-butinyl.

19. A compound according to claim 1, wherein $R^5$ is $C_{1-8}$ alkyl, which is unsubstituted or substituted by halogen, hydroxy, or $S(O)_n R^{11}$ and $R^{11}$ is $C_{1-6}$ alkyl.

20. A compound of Formula I

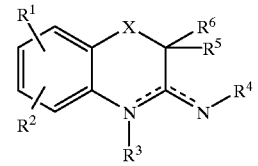

I wherein

is a double bond;

X is —O— or $—S(O)_m—$;

$R^1$ and $R^2$, independently of one another, are each hydrogen, halogen, $S(O)_n—R^7$, $OR^7$, $COOR^7$, $NR^7R^8$, $C(=NR^7)—NHR^8$, $C_{1-6}$ alkyl, $C_{2-6}$ alkenyl, $C_{2-6}$ alkynyl or $—S—C(=NR^7)—NHR^8$;

$R^3$ is hydrogen, $C_{1-12}$ alkyl, phenyl, $CO—NR^9R^{10}$, $CSNR^9R^{10}$, $COR^9$, $CSR^9$, $COOR^9$, OH, or $O—C_{1-6}$ alkyl;

$R^4$ is hydrogen, methyl, ethyl, propyl, isopropyl, n-butyl, sec-pentyl, tert-pentyl, neo-pentyl, n-hexyl, sec-hexyl, heptyl, octyl, $CO—NR^9R^{10}$, $CSNR^9R^{10}$, $COR^9$, $CSR^9$, $COOR^9$, OH, or $O—C_{1-6}$ alkyl;

$R^5$ is halogen, $C_{1-8}$ alkoxy, $S(O)_p—C_{1-6}$ alkyl, $C_{1-8}$ alkylcarbonyl, $C_{1-8}$ alkyl, $C_{3-10}$ cycloalkyl, phenyl or a $C_{1-8}$ alkly radical, which is substituted with phenyl, halogen, hydroxy, $S(O)_n R^{11}$, $NO_2$, $OR^{11}$, $COOR^{11}$, $NR^{11}R^{12}$, cyano, $—C(=NR^{11})—NHR^{12}$ or $—S—C(=NR^{11})—NHR^{12}$;

$R^6$ is hydrogen or $C_{1-3}$ alkyl, which optionally together with $R^5$ forms a 3-, 4- or 5-membered spirocyclic compound;

$R^7$, $R^8$ and $R^{11}$, $R^{12}$, are each, independently, hydrogen, $C_{1-6}$ alkyl, phenyl or $C_{3-7}$ cycloalkyl, $R^9$ and $R^{10}$, independently of one another, are each hydrogen, phenyl, benzyl, $C_{3-7}$ cycloalkyl or $C_{1-6}$ alkyl; and m, n, or p is 0, 1 or 2; or a physiologically compatible salt thereof, with the proviso that when $R^1$, $R^2$, $R^3$, $R^4$ and $R^6$ are each H, $R^5$ is not $C_{1-8}$ alkoxy.

21. A compound of Formula I

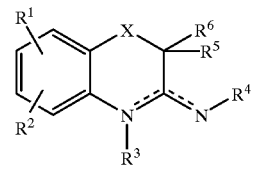

I wherein

is a double bond;

X is $—S(O)_m—$;

$R^1$ and $R^2$, independently of one another, are each hydrogen, halogen, $S(O)_n—R^7$, $OR^7$, $COOR^7$, $NR^7R^8$, $C(=NR^7)—NHR^8$, $C_{1-6}$ alkyl, $C_{2-6}$ alkenyl, $C_{2-6}$ alkynyl or $—S—C(=NR^7)—NHR^8$;

$R^3$ and $R^4$, independently of one another, are hydrogen, $C_{1-12}$ alkyl, phenyl, CO—NR$^9$R$^{10}$, CSNR$^9$R$^{10}$, COR$^9$, CSR$^9$, COOR$^9$, OH, or $O—C_{1-6}$ alkyl;

$R^5$ is halogen, $C_{1-8}$ alkoxy, $S(O)_p—C_{1-6}$ alkyl, $C_{1-8}$ alkylcarbonyl, $C_{1-8}$ alkyl, $C_{3-10}$ cycloalkyl, phenyl or a $C_{1-8}$ alkly radical, which is substituted with phenyl, halogen, hydroxy, $S(O)_n R^{11}$, $NO_2$, $OR^{11}$, $COOR^{11}$, $NR^{11}R^{12}$, cyano, $—C(=NR^{11})—NHR^{12}$ or $—S—C(=NR^{11})—NHR^{12}$;

$R^6$ is hydrogen or $C_{1-3}$ alkyl, which optionally together with $R^5$ forms a 3-, 4- or 5-membered spirocyclic compound;

$R^7$, $R^8$ and $R^{11}$, $R^{12}$, are each, independently, hydrogen, $C_{1-6}$ alkyl, phenyl or $C_{3-7}$ cycloalkyl;

$R^9$ and $R^{10}$, independently of one another, are each hydrogen, phenyl, benzyl, $C_{3-7}$ cycloalkyl or $C_{1-6}$ alkyl; and m, n, or p is 0, 1 or 2; or a physiologically compatible salt thereof, with the proviso that when $R^1$, $R^2$, $R^3$, $R^4$ and $R^6$ are each H, $R^5$ is not $C_{1-8}$ alkoxy.

22. A process for the production of compounds of Formula I, comprising:

a) reacting a compound of Formula IIa or IIb or its salts $$\text{IIa}$$

or $$\text{IIb}$$

wherein $R^1$ and $R^2$, independently of one another, are each hydrogen, halogen, $S(O)_n$—$R^7$, $R^7$, $COOR^7$, $NR^7R^8$, $C(=NR^7)$—$NHR^8$, $C_{1-6}$ alkyl, $C_{2-6}$ alkenyl, $C_{2-6}$ alkynyl or —S—$C(=NR^7)$—$NHR^8$;

$R^7$ and $R^8$, being the same or different, are each hydrogen, $C_{1-6}$ alkyl, phenyl or $C_{3-7}$ cycloalkyl;

X is —O— or —$S(O)_m$—; and

Z is oxygen or sulfur;

with ammonia or a primary or secondary amine; or b) cyclizing a compound of Formula III $$\text{III}$$

wherein $R^1$ and $R^2$ independently of one another, are each hydrogen, halogen, $S(O)_n$—$R^7$, $R^7$, $COOR^7$, $NR^7R^8$, $C(=NR^7)$—$NHR^8$, $C_{1-6}$ alkyl, $C_{2-6}$ alkenyl, $C_{2-6}$ alkynyl or —S—$C(=NR^7)$—$NHR^8$;

$R^5$ is halogen, $C_{1-8}$ alkoxy, $S(O)_p$—$C_{1-6}$ alkyl, $C_{1-8}$ alkylcarbonyl, $C_{1-8}$ alkyl, $C_{3-10}$ cycloalkyl, phenyl or a $C_{1-8}$ alkly radical, which is substituted with phenyl, halogen, hydroxy, $S(O)_nR^{11}$, $NO_2$, $OR^{11}$, $COOR^{11}$, $NR^{11}R^{12}$, cyano, —$C(=NR^{11})$—$NHR^{12}$ or —S—C$(=NR^{11})$—$NHR^{12}$;

$R^6$ is hydrogen or $C_{1-3}$ alkyl, which optionally together with $R^5$ forms a 3-, 4- or 5-membered spirocyclic compound;

$R^7$, $R^8$ and $R^{11}$, $R^{12}$, being the same or different, are each hydrogen, $C_{1-6}$ alkyl, phenyl or $C_{3-7}$ cycloalkyl; and n or p is 0, 1 or 2 and optionally then sulfides are oxidized, esters are saponified, acids are esterified, hydroxy groups are etherified or acylated, amines are acylated, alkylated, diazotized, halogenated, $NO_2$ is introduced or reduced, reacted with thiourea derivatives, the isomers are separated or the salts are formed.

23. A pharmaceutical composition comprising a compound according to claim 1 and a pharmaceutical vehicle.

24. A pharmaceutical composition comprising a compound according to claim 2 and a pharmaceutical vehicle.

25. A pharmaceutical composition comprising a compound according to claim 4 and a pharmaceutical vehicle.

26. A pharmaceutical composition comprising a compound according to claim 5 and a pharmaceutical vehicle.

27. A pharmaceutical composition comprising a compound according to claim 7 and a pharmaceutical vehicle.

28. A pharmaceutical composition comprising a compound according to claim 8 and a pharmaceutical vehicle.

29. A pharmaceutical composition comprising a compound according to claim 9 and a pharmaceutical vehicle.

30. A pharmaceutical composition comprising a compound according to claim 14 and a pharmaceutical vehicle.

31. A pharmaceutical composition comprising a compound according to claim 15 and a pharmaceutical vehicle.

32. A method for treating diseases that are triggered by nitrogen monoxide synthases comprising administering to a patient an effective amount of a compound according to formula (I):

$$\text{I}$$

wherein $\approx\!\!\approx$ is a double bond;

X is —O— or —$S(O)_m$—;

$R^1$ and $R^2$, independently of one another, are each hydrogen, halogen, $S(O)_n$—$R^7$, $OR^7$, $COOR^7$, $NR^7R^8$, $C(=NR^7)$—$NHR^8$, $C_{1-6}$ alkyl, $C_{2-6}$ alkenyl, $C_{2-6}$ alkynyl or —S—$C(=NR^7)$—$NHR^8$;

$R^3$ and $R^4$, independently of one another, are each hydrogen, $C_{1-12}$ alkyl, phenyl, CO—$NR^9R^{10}$, $CSNR^9R^{10}$, $COR^9$, $CSR^9$, $COOR^9$, OH, or O—$C_{1-6}$ alkyl;

$R^5$ is halogen, $C_{1-8}$ alkoxy, $S(O)_p$—$C_{1-6}$ alkyl, $C_{1-8}$ alkylcarbonyl, $C_{1-8}$ alkyl, $C_{3-10}$ cycloalkyl, phenyl or a $C_{1-8}$ alkyl radical, which is substituted with phenyl, halogen, hydroxy, $S(O)_nR^{11}$, $NO_2$, $OR^{11}$, $COOR^{11}$, $NR^{11}R^{12}$, cyano, —$C(=NR^{11})$—$NHR^{12}$ or —S—C$(=NR^{11})$—$NHR^{12}$;

$R^6$ is hydrogen or $C_{1-3}$ alkyl, which optionally together with $R^5$ forms a 3-, 4- or 5-membered spirocyclic compound;

$R^7$, $R^8$ and $R^{11}$, $R^{12}$, being the same or different, are each hydrogen, $C_{1-6}$ alkyl, phenyl or $C_{3-7}$ cycloalkyl;

$R^9$ and $R^{10}$, independently of one another, are each hydrogen, phenyl, benzyl, $C_{3-7}$ cycloalkyl or $C_{1-6}$ alkyl; and m, n, or p is 0, 1 or 2; or a physiologically compatible salt thereof.

33. A method according to claim 32, wherein $R^5$ is halogen, $C_{1-8}$ alkoxy, $S(O)_p$—$C_{1-6}$ alkyl, $C_{1-8}$ alkylcarbonyl, methyl, ethyl, propyl, isopropyl, n-butyl, sec-pentyl, tert-pentyl, neo-pentyl, n-hexyl, sec-hexyl, heptyl, octyl, $C_{3-10}$ cycloalkyl, phenyl or a $C_{1-8}$ alkyl radical, which is substituted with phenyl, halogen, hydroxy, $S(O)_n R^{11}$, $NO_2$, $OR^{11}$, $COOR^{11}$, $NR^{11}R^{12}$, cyano, —C(=$NR^{11}$)—$NHR^{12}$ or —S—C(=$NR^{11}$)—$NHR^{12}$.

34. A method according to claim 32, wherein $R^4$ is hydrogen, methyl, ethyl, propyl, isopropyl, n-butyl, sec-pentyl, tert-pentyl, neo-pentyl, n-hexyl, sec-hexyl, heptyl, octyl, CO—$NR^9R^{10}$, $CSNR^9R^{10}$, $COR^9$, $CSR^9$, $COOR^9$, OH, or O—$C_{1-6}$ alkyl.

35. A method according to claim 32, wherein said compound is:

2,6-Dimethyl-3-amino-1,4-benzoxazine or a physiologically compatible salt thereof;

2,5-Dimethyl-3-amino-1,4-benzoxazine or a physiologically compatible salt thereof;

2,7-Dimethyl-3-amino-1,4-benzoxazine or a physiologically compatible salt thereof;

2,8-Dimethyl-3-amino-1,4-benzoxazine or a physiologically compatible salt thereof;

2-Methyl-2H-3-amino-1,4-benzoxazine or a physiologically compatible salt thereof;

2-Methyl-2H-3-amino-1,4-benzothiazine or a physiologically compatible salt thereof;

2-Ethyl-3-amino-1,4-benzothiazine or a physiologically compatible salt thereof;

2-Ethyl-3-amino-1,4-benzoxazine or a physiologically compatible salt thereof;

2-n-Propyl-3-amino-1,4-benzoxazine or a physiologically compatible salt thereof;

2-Phenyl-2-H-3-amino-1,4-benzoxazine or a physiologically compatible salt thereof;

2-(2-hydroxyethyl)-3-amino-1,4-benzoxazine or a physiologically compatible salt thereof;

2-(2-bromoethyl)-3-amino-1,4-benzoxazine or a physiologically compatible salt thereof; or 2-(2-methylthio-ethyl)-3-amino-1,4-benzoxazine or a physiologically compatible salt thereof.

36. A method according to claim 32, wherein X is —O—.

37. A method according to claim 32, wherein X is —S—.

38. A method according to claim 32, wherein $R^3$, $R^4$, and $R^6$ are each hydrogen.

39. A method according to claim 32, wherein $R^3$ or $R^4$ is hydrogen.

40. A method according to claim 32, wherein $R^6$ is hydrogen.

41. A method according to claim 32, wherein $R^5$ is methyl, ethyl, propyl, isopropyl, n-butyl, sec-pentyl, tert-pentyl, neo-pentyl, n-hexyl, sec-hexyl, heptyl, or octyl.

42. A method according to claim 32, wherein $R^3$, $R^4$, and $R^6$ are each hydrogen.

43. A method according to claim 32, wherein m, n, and p are each zero.

44. A method according to claim 32, wherein $R^5$ and $R^6$ together form spiropropyl, spirobutyl or spiropentyl.

45. A method according to claim 32, wherein said compound is an S-enantiomer.

46. A method according to claim 32, wherein said compound is an R-enantiomer.

* * * * *